US010026505B2

(12) United States Patent
Lack et al.

(10) Patent No.: US 10,026,505 B2
(45) Date of Patent: Jul. 17, 2018

(54) PATIENT SUPPORT WITH DYNAMIC BAR CODE GENERATOR

(71) Applicant: Hill-Rom Services, Inc., Batesville, IN (US)

(72) Inventors: Christopher K. Lack, Milan, IN (US); Steven A. Dixon, Cincinnati, OH (US); Todd P. O'Neal, Fairfield, OH (US); David L. Ribble, Indianapolis, IN (US); Thomas F. Heil, Batesville, IN (US); James M. Allen, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 888 days.

(21) Appl. No.: 14/220,553

(22) Filed: Mar. 20, 2014

(65) Prior Publication Data

US 2014/0296755 A1    Oct. 2, 2014

Related U.S. Application Data (60) Provisional application No. 61/805,358, filed on Mar. 26, 2013.

(51) Int. Cl.
| | |
|---|---|
| *A61G 7/012* | (2006.01) |
| *A61G 7/015* | (2006.01) |
| *A61G 7/05* | (2006.01) |
| *G16H 10/65* | (2018.01) |
| *A61H 1/00* | (2006.01) |
| *A61H 23/04* | (2006.01) |
| *A61G 7/057* | (2006.01) |
| *A61B 5/11* | (2006.01) |
| *A61B 5/00* | (2006.01) |

(52) U.S. Cl.
CPC ............. *G16H 10/65* (2018.01); *A61G 7/012* (2013.01); *A61G 7/0514* (2016.11); *A61G 7/0527* (2016.11); *A61G 7/05776* (2013.01); *A61H 1/001* (2013.01); *A61H 23/04* (2013.01); *A61B 5/1115* (2013.01); *A61B 5/7495* (2013.01); *A61G 2203/16* (2013.01); *A61H 2201/0142* (2013.01); *A61H 2201/0184* (2013.01); *A61H 2201/1238* (2013.01); *A61H 2201/1671* (2013.01); *A61H 2201/501* (2013.01); *A61H 2201/5097* (2013.01); *A61H 2230/06* (2013.01); *A61H 2230/30* (2013.01); *A61H 2230/42* (2013.01); *A61H 2230/50* (2013.01); *A61H 2230/80* (2013.01)

(58) Field of Classification Search
CPC .......... A61G 7/00; A61G 7/012; A61G 7/015; A61G 7/018; A61G 7/05; A61G 7/0506; A61G 7/0507; A61G 7/0527; A61G 7/0528; A61G 13/06; A61G 13/08; A61G 13/10; A61G 2203/20; G06K 7/10821; G06K 7/1095; G06K 19/06037; G06F 19/322; G06F 19/323; G06F 19/327; G06F 19/3406; G06Q 50/22; G06Q 50/24
USPC .......... 5/600, 611, 613, 616, 618, 53.1, 424, 5/425; 235/462.13, 375; 705/2, 3
See application file for complete search history.

(56) References Cited

U.S. PATENT DOCUMENTS

| | | | |
|---|---|---|---|
| 3,439,320 A | | 4/1969 | Ward |
| 4,811,435 A | * | 3/1989 | Foster ..................... A61G 7/05 5/53.1 |

(Continued)

*Primary Examiner* — Robert G Santos
(74) *Attorney, Agent, or Firm* — Barnes & Thornburg LLP (57) ABSTRACT

A care system including a medical device, a mobile computing device, and a information system. The medical device configured to generate data graphics to transfer information from the medical device to the mobile computing device.

19 Claims, 7 Drawing Sheets

(56) References Cited

U.S. PATENT DOCUMENTS

| | | | |
|---|---|---|---|
| 4,857,713 A | 8/1989 | Brown | |
| 5,715,548 A * | 2/1998 | Weismiller | A61G 7/0527 5/611 |
| 5,771,511 A * | 6/1998 | Kummer | A61G 7/015 5/424 |
| 5,781,442 A | 7/1998 | Engleson et al. | |
| 6,163,903 A * | 12/2000 | Weismiller | A61G 7/0527 5/610 |
| 6,279,183 B1 * | 8/2001 | Kummer | A61G 7/015 5/424 |
| 6,336,235 B1 * | 1/2002 | Ruehl | A61G 7/0527 297/354.13 |
| 6,802,450 B2 * | 10/2004 | Cheung | G06K 19/06037 235/462.08 |
| 7,017,208 B2 * | 3/2006 | Weismiller | A61G 7/0528 5/425 |
| 7,028,911 B2 * | 4/2006 | Cheung | G06K 19/06037 235/462.09 |
| 7,154,397 B2 * | 12/2006 | Zerhusen | A47B 23/046 248/276.1 |
| 7,213,279 B2 * | 5/2007 | Weismiller | A61G 7/0528 5/618 |
| 7,237,287 B2 * | 7/2007 | Weismiller | A61G 7/0506 318/16 |
| 7,434,724 B2 * | 10/2008 | Lane | G06F 19/323 235/375 |
| 7,480,951 B2 * | 1/2009 | Weismiller | A61G 7/0528 5/600 |
| 7,568,246 B2 * | 8/2009 | Weismiller | A61G 7/0528 5/424 |
| 7,784,128 B2 * | 8/2010 | Kramer | A61G 7/00 5/613 |
| 7,852,208 B2 * | 12/2010 | Collins, Jr. | A61B 5/1117 340/286.07 |
| 7,868,740 B2 | 1/2011 | McNeely et al. | |
| 7,911,349 B2 | 3/2011 | Zerhusen | |
| 8,065,764 B2 * | 11/2011 | Kramer | A61G 7/00 5/613 |
| 8,284,047 B2 * | 10/2012 | Collins, Jr. | A61B 5/1117 340/3.1 |
| 8,413,274 B2 * | 4/2013 | Weismiller | A61G 7/00 5/624 |
| 8,567,681 B2 * | 10/2013 | Borges | G06K 19/06112 235/462.01 |
| 8,604,917 B2 * | 12/2013 | Collins | A61B 5/1117 340/286.07 |
| 8,616,438 B2 | 12/2013 | Zerhusen | |
| 8,917,166 B2 * | 12/2014 | Collins, Jr. | A61B 5/1117 340/286.07 |
| 9,092,705 B2 * | 7/2015 | Zhuang | G06F 19/3418 |
| 9,183,603 B2 * | 11/2015 | Borges | G06K 19/06112 |
| 9,205,009 B2 * | 12/2015 | Koors | A61G 7/08 |
| 9,367,860 B2 * | 6/2016 | McKirdy | G06Q 30/0271 |
| 9,400,873 B2 * | 7/2016 | Kamen | G06F 19/3418 |
| 9,465,919 B2 * | 10/2016 | Kamen | G06F 19/3418 |
| 9,513,899 B2 * | 12/2016 | Collins, Jr. | A61B 5/1117 |
| 9,530,087 B2 * | 12/2016 | Borges | G06K 19/06112 |
| 9,636,455 B2 * | 5/2017 | Kamen | G06F 19/3418 |
| 9,677,555 B2 * | 6/2017 | Kamen | F04B 43/1261 |
| 9,700,247 B2 * | 7/2017 | Dixon | A61B 5/14552 |
| 9,775,519 B2 * | 10/2017 | Collins, Jr. | A61B 5/002 |
| 9,830,424 B2 * | 11/2017 | Dixon | G06F 19/327 |
| 2002/0044059 A1 * | 4/2002 | Reeder | A61B 5/0002 340/573.1 |
| 2002/0059679 A1 * | 5/2002 | Weismiller | A61G 7/0528 5/610 |
| 2003/0052787 A1 * | 3/2003 | Zerhusen | A47B 23/046 340/573.1 |
| 2004/0026510 A1 * | 2/2004 | Cheung | G06K 19/06037 235/462.1 |
| 2004/0026511 A1 * | 2/2004 | Cheung | G06K 19/06037 235/462.1 |
| 2006/0150332 A1 * | 7/2006 | Weismiller | A61G 7/0528 5/600 |
| 2006/0168729 A1 * | 8/2006 | Weismiller | A61G 7/0528 5/618 |
| 2007/0180618 A1 * | 8/2007 | Weismiller | A61G 7/0528 5/600 |
| 2007/0210917 A1 * | 9/2007 | Collins, Jr. | A61B 5/1117 340/539.1 |
| 2008/0052831 A1 * | 3/2008 | Weismiller | A61G 7/0528 5/616 |
| 2008/0149701 A1 * | 6/2008 | Lane | G06F 19/323 235/375 |
| 2008/0189132 A1 | 8/2008 | Minson et al. | |
| 2008/0300109 A1 | 12/2008 | McKirdy | |
| 2009/0151073 A1 * | 6/2009 | Kramer | A61G 7/0528 5/610 |
| 2010/0001838 A1 * | 1/2010 | Miodownik | G06F 19/327 340/10.1 |
| 2010/0154124 A1 * | 6/2010 | Zerhusen | A47B 23/046 5/658 |
| 2010/0306921 A1 * | 12/2010 | Kramer | A61G 7/0528 5/618 |
| 2011/0074571 A1 * | 3/2011 | Collins, Jr. | A61B 5/1117 340/539.12 |
| 2011/0166891 A1 | 7/2011 | Zerhusen et al. | |
| 2012/0102647 A1 * | 5/2012 | Weismiller | A61G 7/0528 5/601 |
| 2012/0241525 A1 * | 9/2012 | Borges | G06K 19/06112 235/494 |
| 2013/0021143 A1 * | 1/2013 | Collins, Jr. | A61B 5/1117 340/286.07 |
| 2013/0032634 A1 | 2/2013 | McKirdy | |
| 2013/0177455 A1 * | 7/2013 | Kamen | G06F 19/3418 417/313 |
| 2013/0197693 A1 * | 8/2013 | Kamen | G06F 19/3418 700/244 |
| 2013/0204188 A1 * | 8/2013 | Kamen | G06F 19/3418 604/152 |
| 2013/0253291 A1 * | 9/2013 | Dixon | A47C 21/00 600/323 |
| 2014/0048604 A1 * | 2/2014 | Borges | G06K 19/06112 235/462.13 |
| 2014/0091913 A1 * | 4/2014 | Collins, Jr. | A61B 5/1117 340/286.07 |
| 2014/0165290 A1 * | 6/2014 | Koors | A61G 7/08 5/611 |
| 2014/0263616 A1 * | 9/2014 | Zhuang | G06F 19/3418 235/375 |
| 2014/0296755 A1 * | 10/2014 | Lack | A61G 7/0527 601/149 |
| 2015/0081335 A1 * | 3/2015 | Dixon | G06F 19/327 705/3 |
| 2015/0082295 A1 * | 3/2015 | Collins, Jr. | A61B 5/1117 717/170 |
| 2016/0042264 A1 * | 2/2016 | Borges | G06K 19/06112 235/375 |
| 2016/0140307 A1 * | 5/2016 | Brosnan | G06F 19/3406 600/324 |
| 2016/0203292 A1 * | 7/2016 | Kamen | G06F 19/3418 700/237 |
| 2016/0338891 A1 * | 11/2016 | Agdeppa | A61G 7/05 |
| 2017/0011202 A1 * | 1/2017 | Kamen | G06F 19/3418 |
| 2017/0035295 A1 * | 2/2017 | Collins, Jr. | A61B 5/1117 |
| 2017/0061096 A1 * | 3/2017 | Kelly | G06F 19/3468 |
| 2017/0181909 A1 * | 6/2017 | Baker, Jr. | A61G 7/052 |
| 2017/0228684 A1 * | 8/2017 | Perry | G06Q 10/06311 |
| 2017/0242969 A1 * | 8/2017 | Baudet | G06F 19/3412 |
| 2017/0316160 A9 * | 11/2017 | Herbst | G06Q 10/10 |
| 2017/0367577 A1 * | 12/2017 | Collins, Jr. | G06F 19/3412 |
| 2018/0039743 A1 * | 2/2018 | Dixon | A61G 7/05 |

* cited by examiner

PATIENT SUPPORT WITH DYNAMIC BAR CODE GENERATOR

This application claims the benefit, under 35 U.S.C. § 119(e), of U.S. Provisional Application No. 61/805,358, which was filed Mar. 26, 2013, and which is hereby incorporated by reference herein in its entirety

BACKGROUND

The present disclosure is related to patient supports. More specifically, the present disclosure is related to patient supports including a graphic display.

Some patient supports include graphic displays such as liquid crystal displays (LCDs) or plasma displays. These graphic displays may show information about the patient support and/or about a patient associated with the patient support to a user checking in at the patient support. The information available to the user checking in at the patient support may not be available to users who are not in viewing distance of the display and may not be recorded for later review and analysis.

SUMMARY

The present application discloses one or more of the features recited in the appended claims and/or the following features which, alone or in any combination, may comprise patentable subject matter:

According to the present disclosure, a patient support system may include a reconfigurable patient support apparatus, and a control system. The control system may include a controller and a display coupled to the controller.

In some embodiments, the controller may be configured to generate a data graphic. The data graphic may include information corresponding to the configuration of the patient support apparatus and to display the data graphic on the display.

In some embodiments, the patient support apparatus may include a lower frame, an upper frame, and a lift system coupled between the lower frame and the upper frame. The lift system may be configured to move the upper frame relative to the lower frame. The data graphic may include information corresponding to the position of the upper frame relative to the lower frame.

In some embodiments, the patient support apparatus may include a deck. The deck may include a seat deck section coupled to the upper frame and a head deck section movable from a first position to a second position relative to the seat deck section. The data graphic may include information corresponding to the position of the head deck section relative to the seat deck section.

In some embodiments, the patient support apparatus may include a siderail and movable from a raised position to a lowered position. The data graphic may include information corresponding to the position of the siderail.

In some embodiments, the patient support apparatus may include a headrail coupled to the head deck section and movable from a raised position to a lowered position relative to the head deck section. The data graphic may include information corresponding to the position of the headrail relative to the head deck section.

In some embodiments, the patient support apparatus may include a footboard movable between a first position coupled to the deck and a second position spaced apart from the deck. The data graphic may include information corresponding to the position of the footboard relative to the deck.

In some embodiments, the patient support apparatus may include a plurality of wheels and a brake system movable from a braked position resisting movement of at least one wheel to an unbraked position allowing movement of at least one wheel. The data graphic includes information corresponding to the position of the brake system.

In some embodiments, the patient support apparatus may include at least one sensor configured to detect patient data corresponding to a patient supported on the patient support apparatus. The data graphic may include information corresponding to the patient data. The at least one sensor may include a scale coupled to the controller and configured to detect patient weight of a patient on the patient support apparatus. The data graphic may include information corresponding to the patient weight.

In some embodiments, the data graphic may be a matrix barcode. The data graphic may be a quick response code.

According to another aspect of the present disclosure, a patient support system may include a patient support surface, a pressurized air source, and a control system. The patient support surface may include a plurality of inflatable bladders. The pressurized air source may be coupled to the patient support surface and configured to provide pressurized air to the plurality of inflatable bladders of the patient support surface. The control system may include a controller and a display coupled to the controller.

In some embodiments, the controller may be configured to generate a data graphic. The data graphic may include information corresponding to the status of the plurality of air bladders.

In some embodiments, the plurality of inflatable bladders may include a left and a right turn bladder configured to rotate a patient on the patient support surface about an axis extending from a head end to a foot end of the patient support surface to provide rotation therapy to the patient. The data graphic may include information corresponding to rotation therapy provided to a patient.

In some embodiments, the plurality of inflatable bladders may include a set of vibration bladders configured to be quickly inflated and deflated under a patient on the support surface to provide vibration therapy to the patient. The data graphic may include information corresponding to the vibration therapy provided to a patient.

In some embodiments, the patient support surface may include a topper arranged to extend along a top surface of the patient support surface and configured to conduct air from the pressurized air source along the top surface of the patient support surface. The data graphic may include information corresponding to the conduction of air along the top surface of the patient support surface.

In some embodiments, the data graphic may be a matrix barcode. The data graphic may be a quick response code.

According to another aspect of the present disclosure, a patient support system may include a patient support apparatus and a control system. The control system may include a controller, a user input coupled to the controller, and a display coupled to the controller.

In some embodiments, the controller may be configured to receive information from the user input. The controller may be further configured to generate a data graphic including the information from the user input and to display the data graphic on the display. In some embodiments, the data graphic may be a matrix barcode.

In some embodiments, the information from the user input may correspond to a patient supported on the patient support apparatus. The information from the user input may include at least one of patient pain level, patient respiratory rate, patient heart rate, patient current medications, and patient blood pressure.

According to the another aspect of the present disclosure, a care system may include a patient support system, a care system server, and a data graphic reader. The patient support system may include a patient support apparatus and a control system coupled to the patient support apparatus. The care system server may be spaced apart from the patient support system.

In some embodiments, the control system may include a display and controller configured to generate a data graphic including information corresponding to a status of the patient support apparatus and to display the data graphic on the display. The data graphic reader may be configured to receive information from the data graphic and to communicate the information to the care system server. In some embodiments, the status of the patient support apparatus may include at least one of patient support apparatus height, deck position, siderail position, headrail position, and brake position.

In some embodiments, the care system may include a patient support surface mounted on the patient support apparatus. The patient support surface may include a plurality of inflatable bladders and a pressurized air source coupled to the plurality of inflatable bladders. The data graphic may include information corresponding to the status of at least one of the inflatable bladders.

In some embodiments, patient support surface may include a topper arranged to extend along a top surface of the patient support surface and configured to conduct air from the pressurized air source along the top surface of the patient support surface. The data graphic may include information corresponding to the conduction of air along the top surface of the patient support surface.

In some embodiments, the patient support apparatus may include at least one sensor configured to detect patient data corresponding to a patient supported on the patient support apparatus. The data graphic may include information corresponding to the patient data.

In some embodiments, the data graphic reader may be one of a scanner, a tablet computer, and a mobile phone. The data graphic may be a matrix barcode.

According to another aspect of the present disclosure, a medical device may include a reconfigurable therapeutic apparatus, and a control system. The control system may include a controller and a display coupled to the controller.

In some embodiments, the controller may be configured to generate a data graphic including information corresponding to the configuration of the therapeutic apparatus. The controller may be further configured to display the data graphic on the display. In some embodiments, the data graphic may be a matrix barcode.

In some embodiments, the medical device may include at least one sensor configured to detect patient data. The data graphic may include information corresponding to the patient data.

According to another aspect of the present disclosure, a care system may include a medical device, a care system server, and a data graphic reader. The medical device may include a reconfigurable therapeutic apparatus and a control system. The care system server may be spaced apart from the medical device In some embodiments, the control system may include a controller and a display coupled to the controller. The controller may be configured to generate a data graphic including information corresponding to the configuration of the therapeutic apparatus and to display the data graphic on the display.

In some embodiments, the data graphic reader may be configured to receive information from the data graphic and to communicate the information to the care system server. The data graphic may be a matrix barcode.

In some embodiments, the medical device may include at least one sensor configured to detect patient data corresponding to a patient associated with the medical device. The data graphic may include information corresponding to the patient data.

In some embodiments, the control system may include a user input coupled to the controller and configured to receive data from a user. The data graphic may include information corresponding to the data received by the controller from the user.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
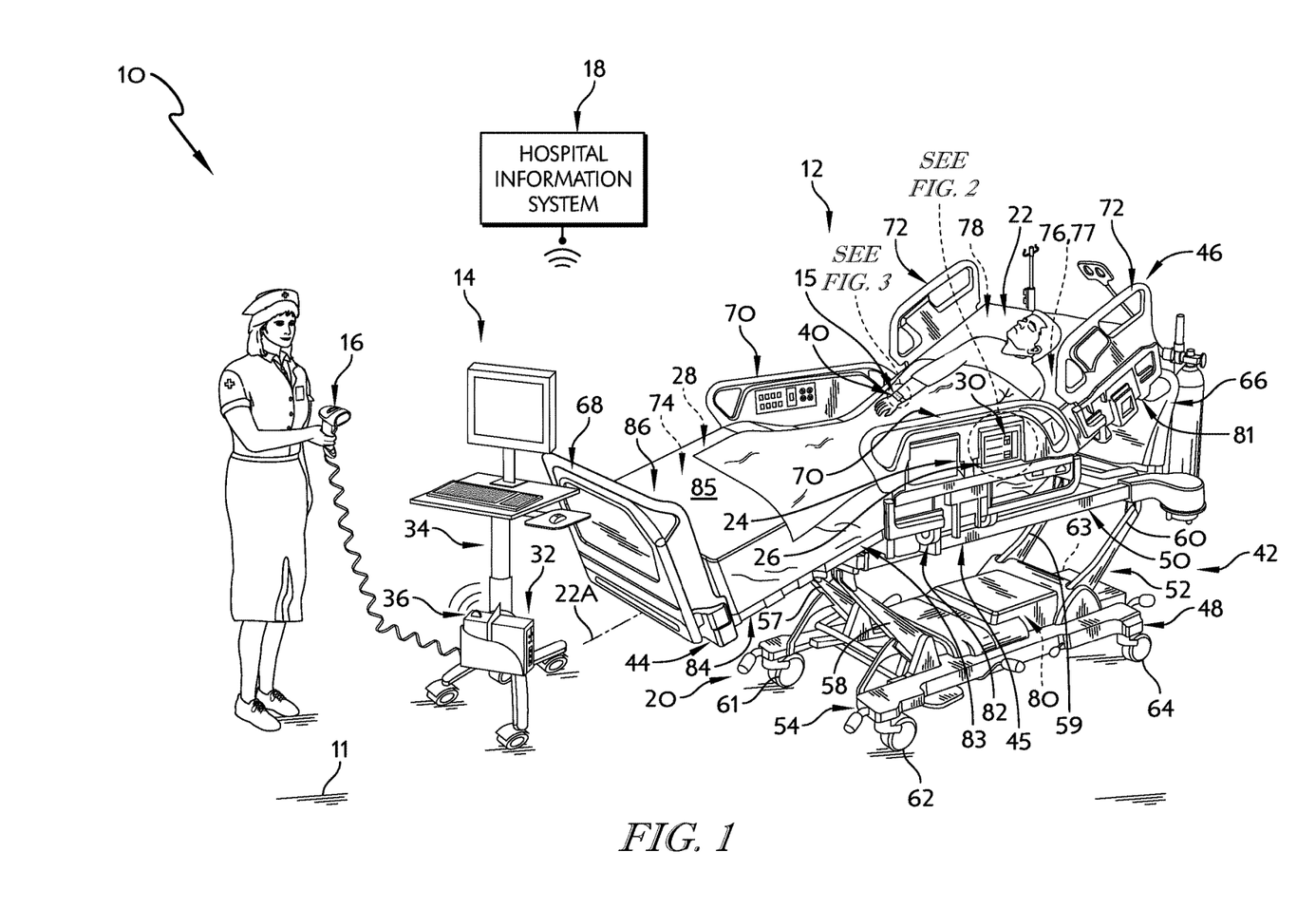
FIG. 1 is a perspective view of a care system including a patient support system, a mobile computing device, and a information system configured to employ dynamically generated data graphics to transfer information from the patient support system to the mobile computing device.

A care system 10 illustratively includes a patient support system 12, a mobile computing device 14 with a reader 16, and a information system 18 as shown in FIG. 1. The patient support system (sometimes called a patient bed or hospital bed) 12 is a medical device configured to support and provide therapies to a patient in a care setting. The mobile computing device 14 is illustratively used to collect real-time information associated with a patient (illustratively from a patient bracelet 15) and real-time information associated with the patient support system 12 via the reader 16. The mobile computing device 14 is then configured to communicate the collected information to the information system (sometimes called server) 18 as suggested in FIG. 4.

The patient support system 12 illustratively includes a patient support apparatus 20, a patient support surface 22, and a control system 24 with a touch-screen display 26. The patient support apparatus (sometimes called a bed frame) 20 is reconfigurable to support a patient at a variety of heights and positions relative to an underlying floor 11. The patient support surface (sometimes called a mattress) 22 includes a plurality of inflatable bladders 28 that support a patient at various firmness levels and that provide therapies to a patient. The control system 24 illustratively controls the operation of both the patient support apparatus 20 and the patient support surface 22. In some embodiments, two or more controllers may used to control the patient support apparatus 20 and the patient support surface 22.

Figure 3:
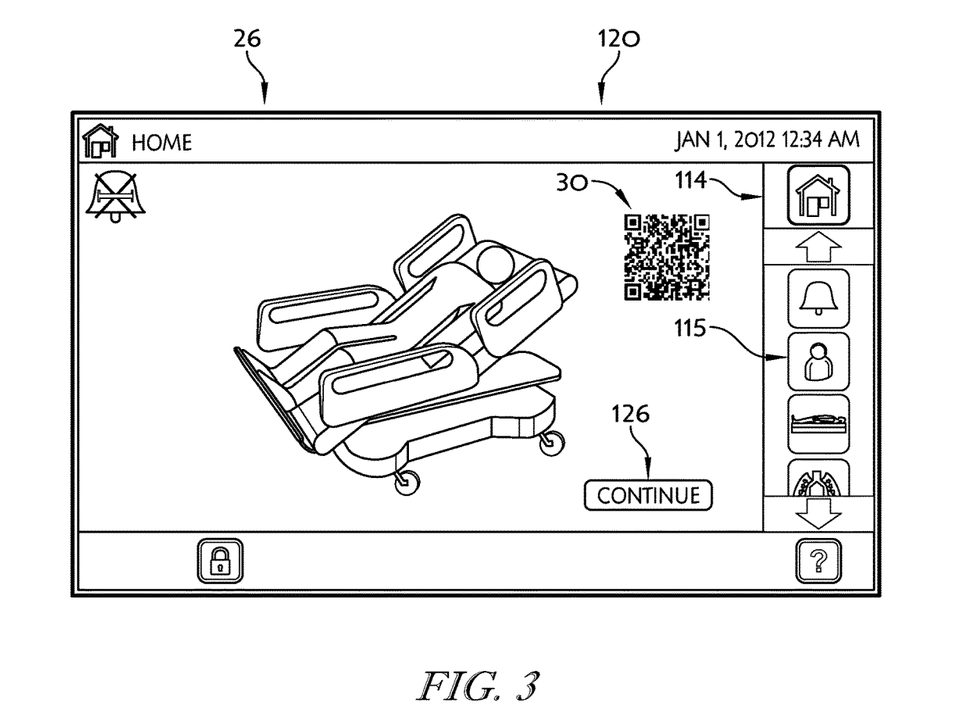
FIG. 3 is a detail view of a display included in the patient support system with a dynamicly generated data graphic embodied as a quick response (QR) bar code.

The control system 24 is configured to dynamically generate and display a data graphic 30 on the display 26 so that information associated with the patient support system 12 can be collected by the mobile computing device 14 as shown in FIG. 3. The dynamic data graphic 30 includes a variety of information corresponding to the patient support apparatus 20 and the patient support surface 22. The illustrative data graphics 30, 40 are optical machine-readable quick response (QR) codes configured to include relatively large amounts of information in a relatively small spaces on the display 26 when compared to text. In some embodiments, the data graphics 30, 40 may be other matrix (two-dimensional) bar codes, linear (one-dimensional) bar codes, or a mix of bar code styles. The bar codes used may be industry-standard and/or proprietary in format. The bar codes used may be black-and-white or may include color. In some embodiments, other types of optical machine-readable data containing graphics, such as dataglyph barcodes, may also be used.

Information about the configuration of the patient support apparatus 20 and information about the firmness and/or therapy performance of the patient support surface 22 are included in the data graphic 30. In some embodiments, the dynamic data graphic 30 may also include information corresponding to the location of the patient support system 12 and information corresponding to a patient supported on the patient support system 12.

Figure 2:
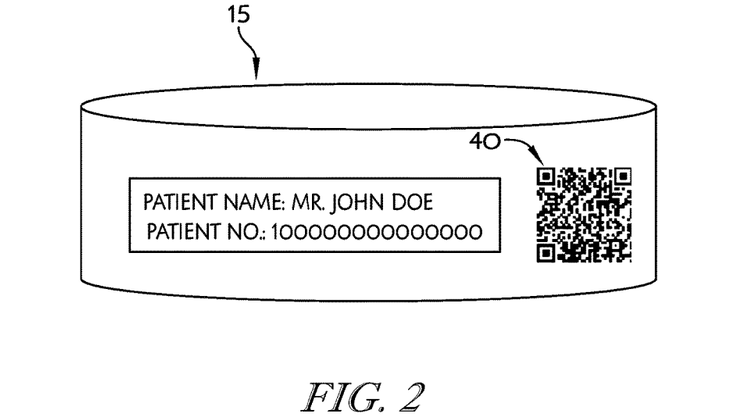
FIG. 2 is a detail perspective view of a patient identification bracelet including a static data graphic embodied as a quick response (QR) bar code.

Patient information corresponding to a patient supported on the patient support system 12 is stored in a static data graphic 40 printed on the patient bracelet 15 as shown in FIG. 2. In the illustrative embodiment, patient information includes a patient's name and an assigned patient number. The mobile computing device 14 is configured to associate information from the static data graphic 40 with the information included in the dynamic data graphic 30 and to send a combined information packet to the information system 18 for addition to the patient's electronic medical record. In some embodiments, the combined information packet may be stored in the mobile computing device and may be added to a partial or full electronic medical record for the patient housed in the mobile computing device 14.

The mobile computing device 14 illustratively includes the reader 16, a computer 32, and a wheeled cart 34 cooperating to provide a computer on wheels as shown in FIG. 1. The reader 16 is illustratively an optical scanner but in other embodiments may be a web cam or another optical sensor. The computer 32 is illustratively a desktop-style personal computer that communicates with the information system 18 via a wi/fi enabled transceiver 36. In some embodiments, the computer 32 may communicate with the information system 18 via the transceiver 36 over other wireless or wired communication networks. In some embodiments, other mobile computing devices 14 may be used in addition to, or in place of, the computer on wheels shown in FIG. 1; for example, smart phones with cameras, tablet computers with cameras, smart scanners, or other mobile devices with optical readers may be used in the care system 10.

The illustrative patient support apparatus 20 is operable to raise, lower, reposition, and contain a patient as suggested in FIG. 1. The patient support apparatus 20 includes a base 42, a deck 44, and a containment system 46 as shown in FIG. 1. The base 42 is configured to raise and lower a patient on the patient support apparatus 20 relative to the floor 11. The base 42 is also configured to verify that a patient is supported on the patient support apparatus 20 and to weigh the patient via a scale 45 incorporated into the base 42. The deck 44 includes articulated sections that are movable to support a patient in a variety of positions including a lie-flat position, a sit-up position, and a chair-egress position. The containment system 46 extends up around the deck 44 and blocks inadvertent patient exit from the patient support apparatus 20.

The base 42 illustratively includes a lower frame 48, an upper frame 50, a lift system 52, and a brake system 54 as shown in FIG. 1. The lift system 52 is includes pivotable legs 57-60 configured to raise and lower the upper frame 50 relative to the lower frame 48. The brake system 54 is configured to brake and unbrake wheels 61-64 included in the lower frame 48.

The deck 44 illustratively includes a head deck section 81, a seat deck section 82, a thigh deck section 83, and a foot deck section 84 as shown in FIG. 1. The head deck section 81 is illustratively movable relative to the seat deck section 82 and the upper frame 50 to form an angle relative to the upper frame 50. The seat deck section 82 is coupled to the upper frame 50 for movement therewith. The thigh deck section 83 is coupled to the seat deck section 82 to pivot relative thereto. The foot deck section 84 is coupled to the thigh deck section 83 to pivot relative thereto. The deck 44 also includes a plurality of sensors (not shown) coupled to the control system 24 to report the position of the deck sections 81, 82, 83, 84.

The scale 45 is illustratively includes a plurality of load cells (not shown) coupled between the upper frame 50 of the base 42 and the deck 44 as suggested in FIG. 1. The scale 45 is coupled to the control system 24 and is configured to detect patient weight when a patient is on the patient support apparatus 20. The control system 24 is configured to determine if a patient is on the patient support apparatus 20 based on the weight from the scale 45 and to provide an out-of-bed alarm function that can be set to trigger when a patient gets up from the patient support apparatus 20. In some embodiments, the scale 45 may be included as part of a patient position monitoring system such as the system described in U.S. Pat. No. 7,437,787, which is hereby incorporated herein by reference.

The containment system 46 illustratively includes a headboard 66, a footboard 68, siderails 70, and headrails 72 as shown in FIG. 1. The footboard 68, siderails 70, and headrails 72 are coupled to the control system 24 to report their position to the control system 24. The footboard 68 is removably coupled to the deck 44 and moves from an installed to a removed position. The siderails 70 are coupled to the upper frame 50 and are movable between a raised position and a lowered position. The headrails 72 are coupled to the head deck section 81 for movement therewith and are movable between a raised position and a lowered position.

The patient support surface 22 is configured to support a patient at various firmness levels and to provide therapies to the patient when supported on the patient support system 12. The plurality of inflatable bladders 28 included in the patient support surface 22 illustratively include a plurality of support bladders 74, left and right lateral rotation bladders 76, 77, and percussion and vibration bladders 78 to support and provide therapies to a patient on the patient support surface 22. The inflatable bladders 74, 76, 77, 78 (and other components) of the support surface 22 are described and shown in detail in U.S. application Ser. No. 13/828,186 filed on Mar. 14, 2013 which is incorporated herein by reference in its entirety, except where it explicitly conflicts with the description and drawings of the present disclosure. In some embodiments, the support surface 22 may be of the type described in U.S. Provisional Application No. 61/778,789 filed on Mar. 13, 2013 and configured to support and provide therapies to a patient supported on the support surface 22.

The support bladders 74 are inflated to select firmness for the support surface 22. The lateral rotation bladders 76, 77 are inflatable to rotate a patient about a longitudinal axis 22A of the patient support surface 22 and are configured to provide rotation therapy to a patient on the support surface 22. The percussion and vibration bladders 78 are configured to be quickly inflated and deflated under a patient on the support surface to provide vibration therapy to the patient on the support surface 22. Each inflatable bladder 74, 76, 77, 78 is coupled to an air system 80 housed in the patient support apparatus 20 that is configured to inflate and deflate the bladders 74, 76, 78 as directed by the control system 24. Pressure sensors (not shown) included in the air system 80 are coupled to the inflatable bladders 74, 76, 77, 78 and to the control system 24. These pressure sensors are configured to detect the pressures in the bladders 74, 76, 77, 78 to report bladder status and surface therapy status.

The illustrative patient support surface 22 also includes a topper 86 arranged to extend along a top surface 85 of the patient support surface 22 and to conduct air along the top surface 85 of the patient support surface 22. The illustrative topper is coupled to the air system 80 to receive pressurized air. The air system 80 includes pressure sensors (not shown) configured to detect air being supplied to the topper 86 and to report topper therapy status to the control system 24.

Figure 4:
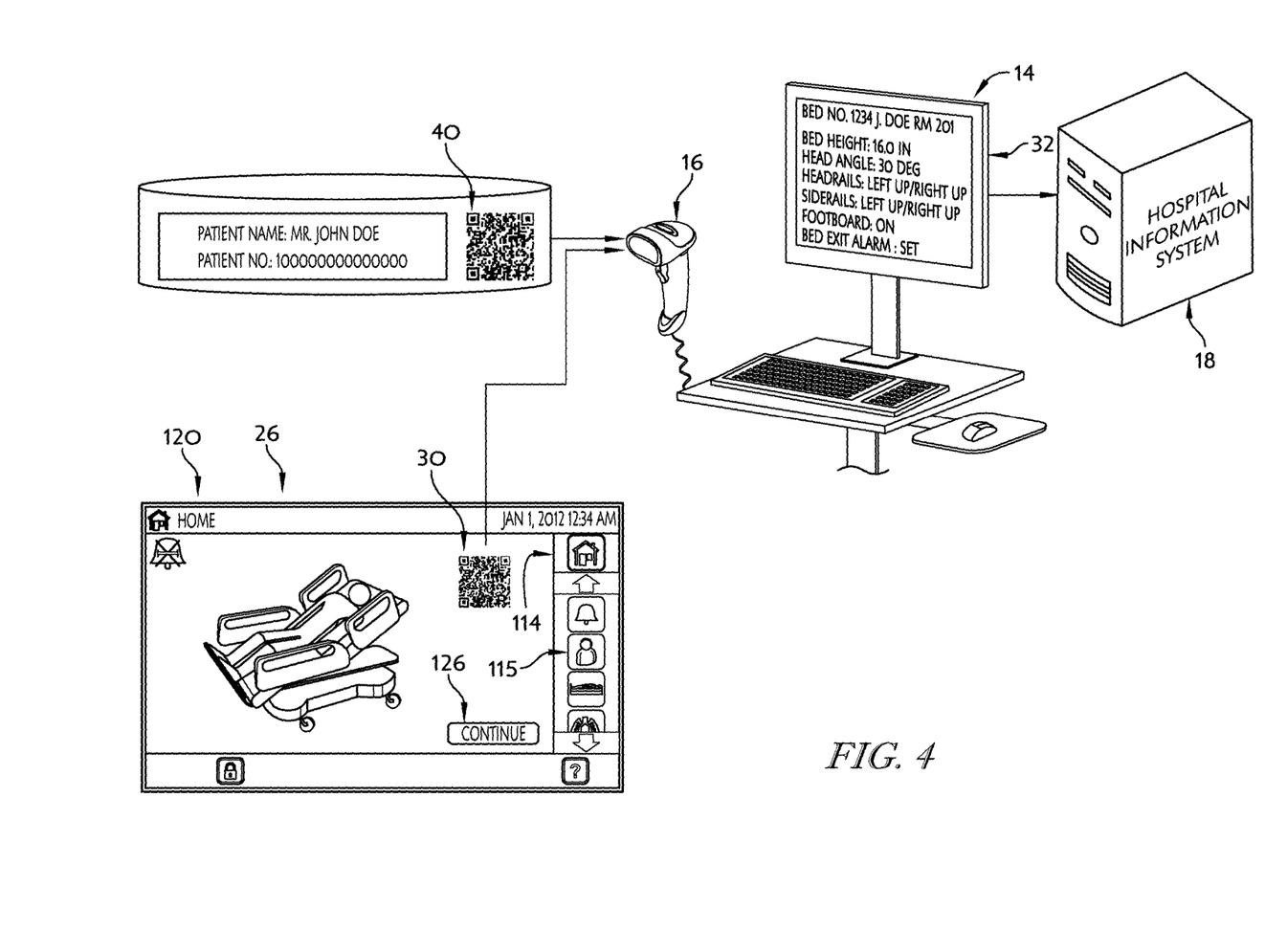
FIG. 4 is a graphic flow diagram showing that information from the static and dynamic data graphics included in the patient identification bracelet and the display are collected and sent to the information system via the mobile computing device.

In operation, information corresponding to the patient support system 12 and a patient supported on the patient support system 12 is collected by the mobile computing device 14 as suggested in FIG. 4. To collect the information, the reader 16 is used to scan both the dynamic data graphic 30 presented on the display 26 and the static data graphic 40 presented on the patient identification bracelet 40. The collected information is then communicated to the information system 18 for addition to the patient's electronic medical record which can then be analyzed with respect to patient outcomes and/or caregiver adherence to protocols (for example, analyzing if patient support systems are being properly configured by caregivers).

Using a data collection system including the mobile computing device 14 may be helpful in care centers that do not connect patient support systems 12 to internal networks (wired or wireless) and/or to care centers that do not have internal networks connecting information systems 18 to care locations (rooms/bays). The system may also be helpful when implemented in other medical devices used in care systems such as fluid pumps, heart rate monitors, respiration monitors, pulmonary therapy devices, blood pressure cuffs, temperature probes, or other care center devices. The care system 10 may include one or more such medical devices configured to dynamically generate data graphics including information to be transferred to the mobile computing device 14 and to the information system 18.

In some embodiments, the display 26 may be a non-touchscreen display and used with other inputs, for example buttons, switches, pedals, etc. connected to the control system 24. In some embodiments, the display 26 may be sized to show only the dynamically generated data graphic 30.

Figure 5:
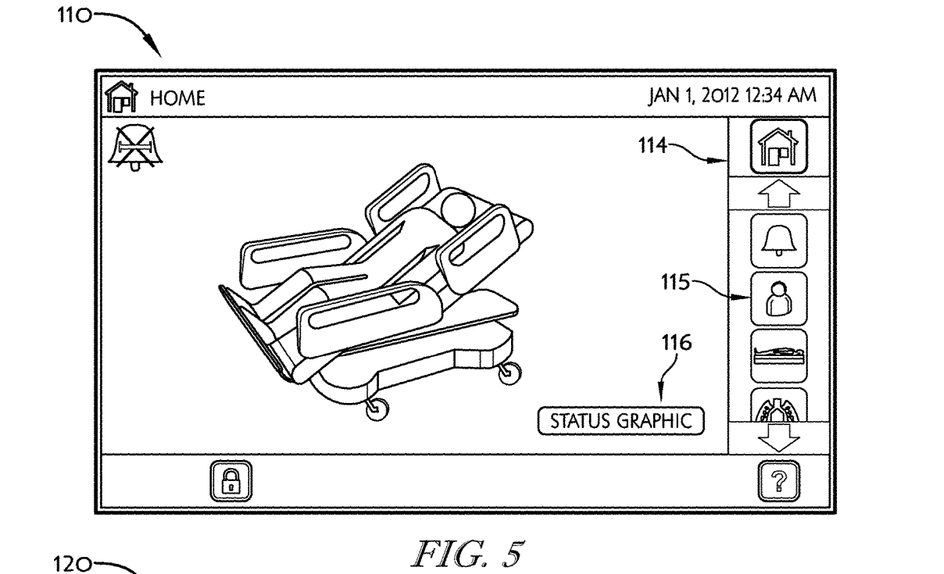
FIG. 5 is a home screen with a status graphic button that is presented on the display included in the patient support system.
Figure 6:
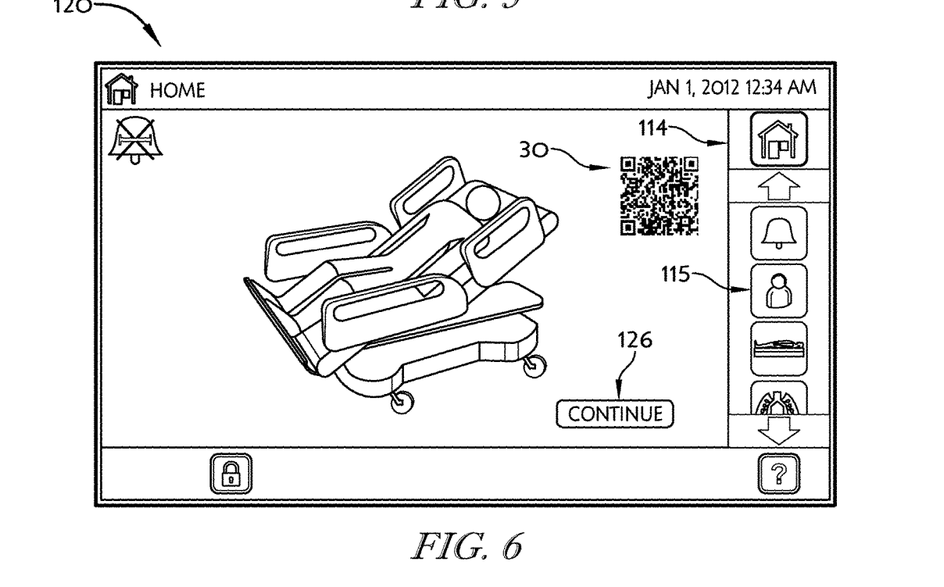
FIG. 6 is a home-status screen with a dynamically generated data graphic that is presented on the display included in the patient support system in response to a user pressing the status graphic button shown in FIG. 5.

Turning now to FIGS. 5 and 6, a home screen 110 and a home-status screen 120 that are displayed on the display 26 by the control system 24 are shown. The control system 24 is illustratively configured to aggregate information about the patient support system 12 and any known information about a patient on the patient support system 12 in response to receiving a signal that a status button 116 has been pressed. The aggregated information is then used by the control system 24 to dynamically generate the data graphic 30. The dynamic data graphic 30 (once generated) is displayed on the home-status screen 120 for scanning by the reader 16 as shown in FIG. 6. In some embodiments, the dynamic data graphic 30 may be regularly updated and displayed on the home screen 110 rather than requiring a button press by a user.

The information regarding the patient support system 12 illustratively included in the data graphic 30 may correspond to the status of the patient support apparatus 20 and the patient support surface 22. More particularly, with regard to the patient support apparatus 20, the data graphic 30 may include, among other things, information corresponding to the position of the upper frame 50 relative to the lower frame 48, the position of the movable deck sections 81, 83, 84, the position of the siderails 70, the position of the headrails 72 relative to the head deck section 81, the position of the footboard 68 relative to the deck 44, the position of the brake system 54, and/or whether or not an out-of bed or other alarm is set. With regard to the patient support surface 22, the data graphic may include information corresponding to the status of the plurality of air bladders 28, rotation therapy provided to a patient by the rotation bladders 76, 77, vibration therapy provided to a patient by the percussion and vibration bladders 78, and/or the conduction of air along the top surface of the patient support surface by the topper 86.

In some embodiments, location information corresponding to the location of the patient support system 12 (room/bay number) may also be included in the dynamic data graphic 30 as suggested in FIG. 4. Location information is illustratively input into control system 24 by a user. In some embodiments, location information may be detected by the patient support system 12 via a location detection system included in the patient support system 12. For example, a location system similar to that taught in U.S. patent application Ser. No. 13/216,341 filed Aug. 24, 2011, may be include in the patient support system 12 and the care system 10. U.S. patent application Ser. No. 13/216,341 is hereby incorporated herein by reference. In some embodiments, the control system 24 may include global positioning sensors or other locating systems.

Patient information from the static data graphic 40 illustratively includes, among other things, patient name, patient identification number, admission date, and age. In some embodiments, additional information recorded at admission is embedded in the static data graphic 40 such as current medications, reason for visit, symptoms, and the like.

Figure 7:
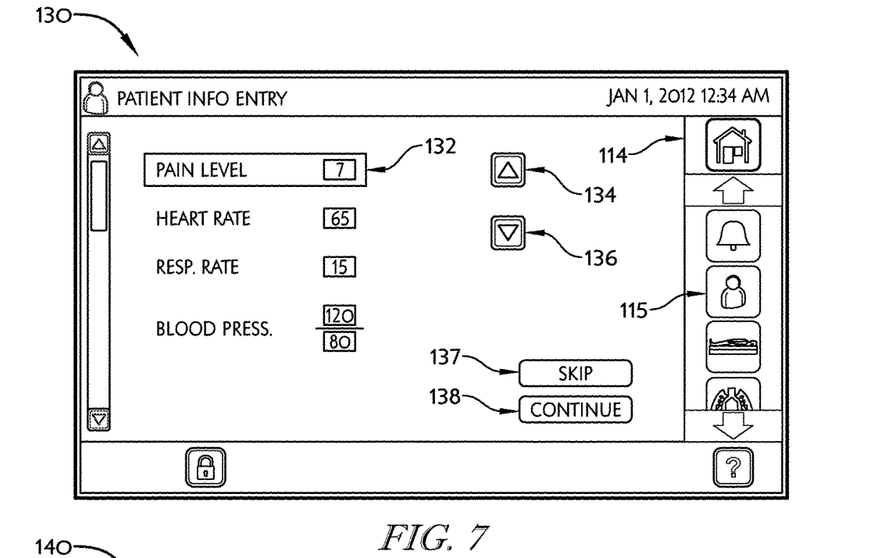
FIG. 7 is a patient information entry screen that is presented on the display included in the patient support system.
Figure 8:
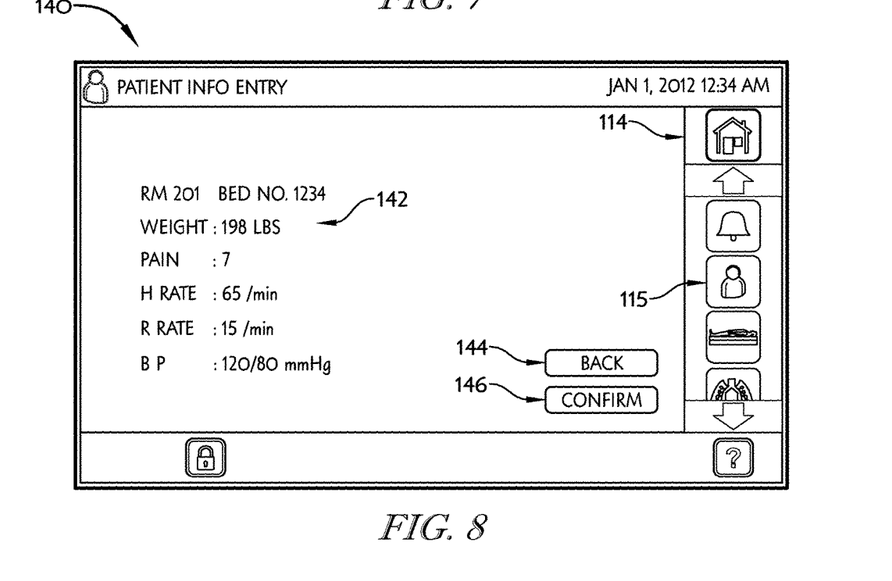
FIG. 8 is a patient information entry-confirmation screen that is presented on the display included in the patient support system.

Patient information may also be included in the dynamic data graphic 30 both from patient sensors included in the patient support system 12 and from user input to the control system 24 as suggested in FIGS. 7 and 8. Illustratively, the dynamic data graphic 30 includes patient weight from the scale 45. The dynamic data graphic 30 may also include pain level, heart rate, respiration rate, and blood pressure as entered by a user via patient information entry screens 130, 140 as shown in FIGS. 7 and 8.

Figure 9:
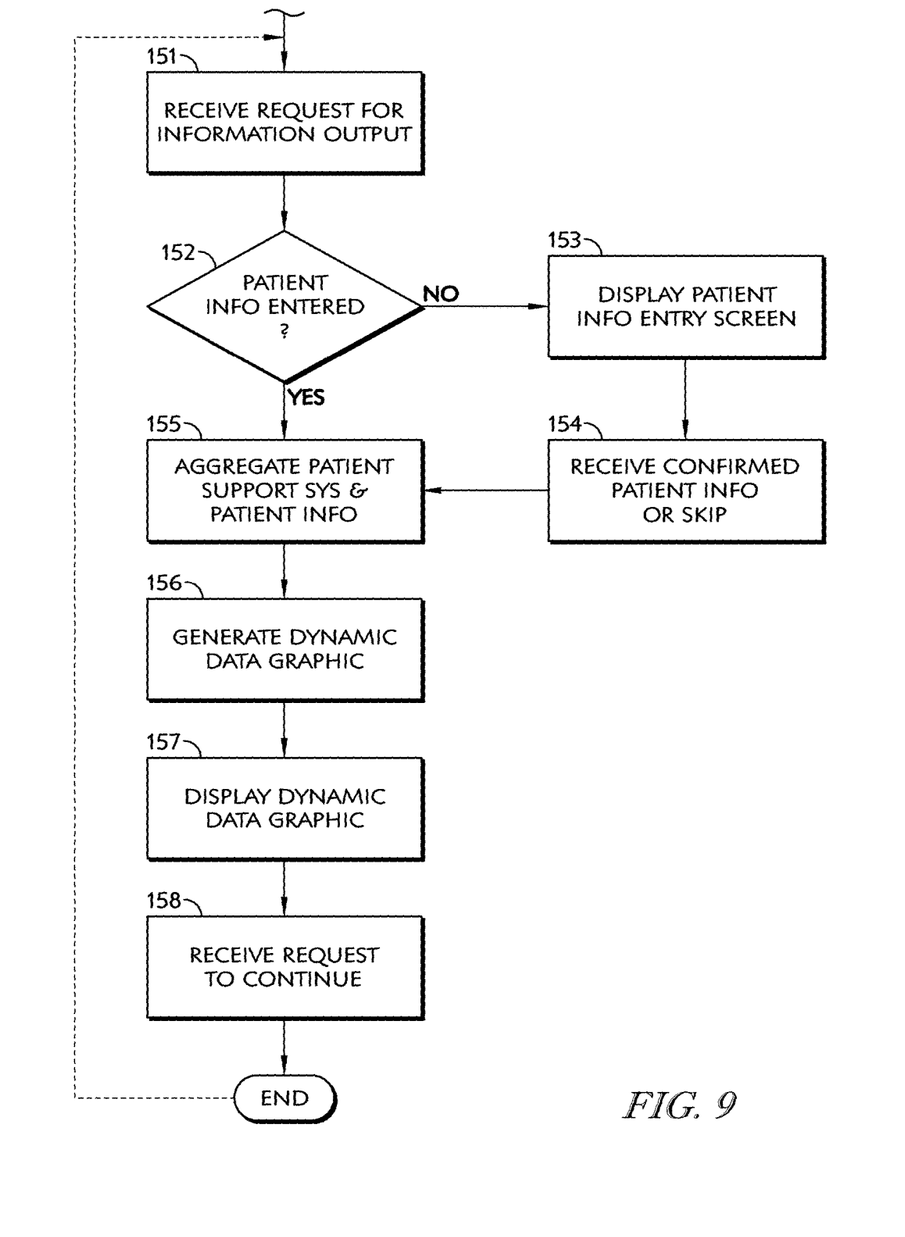
FIG. 9 is a block diagram showing a program executed by a control system included in the patient support system of FIG. 1.

The control system 24 includes memory containing program instructions and a processor configured to execute the program instructions from the memory. The control system 24 is illustratively configured to perform a program 150 as shown in FIG. 9. The program 150 includes a first step 151 in which the control system receives a request for information output. The request for information output is illustratively generated in response to a user pressing the status graphic button 116 included in the home screen 110 shown in FIG. 5.

The program 150 then proceeds to a decision step 152 in which the control system 24 determines if patient information has been entered within a predetermined time frame into the control system via the patient information entry screens shown in FIGS. 7 and 8. If patient information has not been received, the control system 24 displays the patient information entry screen 130, shown in FIG. 7, in a step 153. The patient information entry screen 130 includes a list of patient characteristics 132 to be entered and arrows 134, 136 for adjusting the patient characteristic values. The patient information entry screen 130 may be displayed at any time by a user selecting an icon 115 from a menu 114 included in the home screen 110. When values are entered and a continue button 138 is pressed by a user, the program advances to a step 154 in which the updated patient information is confirmed. The patient information entry screen 130 also includes a skip button 137 that allows a user to skip entry of patient information that allows a user to skip ahead in the program 150 to a step 155.

In step 154, a patient information entry-confirmation screen 140 is displayed and a user can see the entered patient information in a list 142 and can confirm the information or go back to screen 130 via buttons 144, 146 as shown in FIG. 8. Once patient information is entered and confirmed (or entry is skipped), the program 150 advances to the step 155 as shown in FIG. 9.

If patient information has been received within the predetermined time frame, the control system 24 aggregates the information corresponding to the patient support system 12 and to a patient on the patient support system 12 in the step 155. From the aggregated information, the control system 24 generates the dynamic data graphic 30 in a step 156 and then displays the dynamic data graphic 30 on the display 26 (as shown in FIG. 6) in a step 157. The control system 24 then removes the generated data graphic 30 when a user presses a continue button 126 included in the home-status screen 120 in a step 158.

In some embodiments, more than one dynamic data graphic may be generated by the control system 24. For example, dynamic data graphics with information corresponding to one or more of the patient support apparatus 20, the patient support surface 22, the therapies applied to a patient on the patient support system 12, and/or a patient associated with the patient support system 12 may be independently generated and displayed for collection by the mobile computing device 14.

Figure 10:
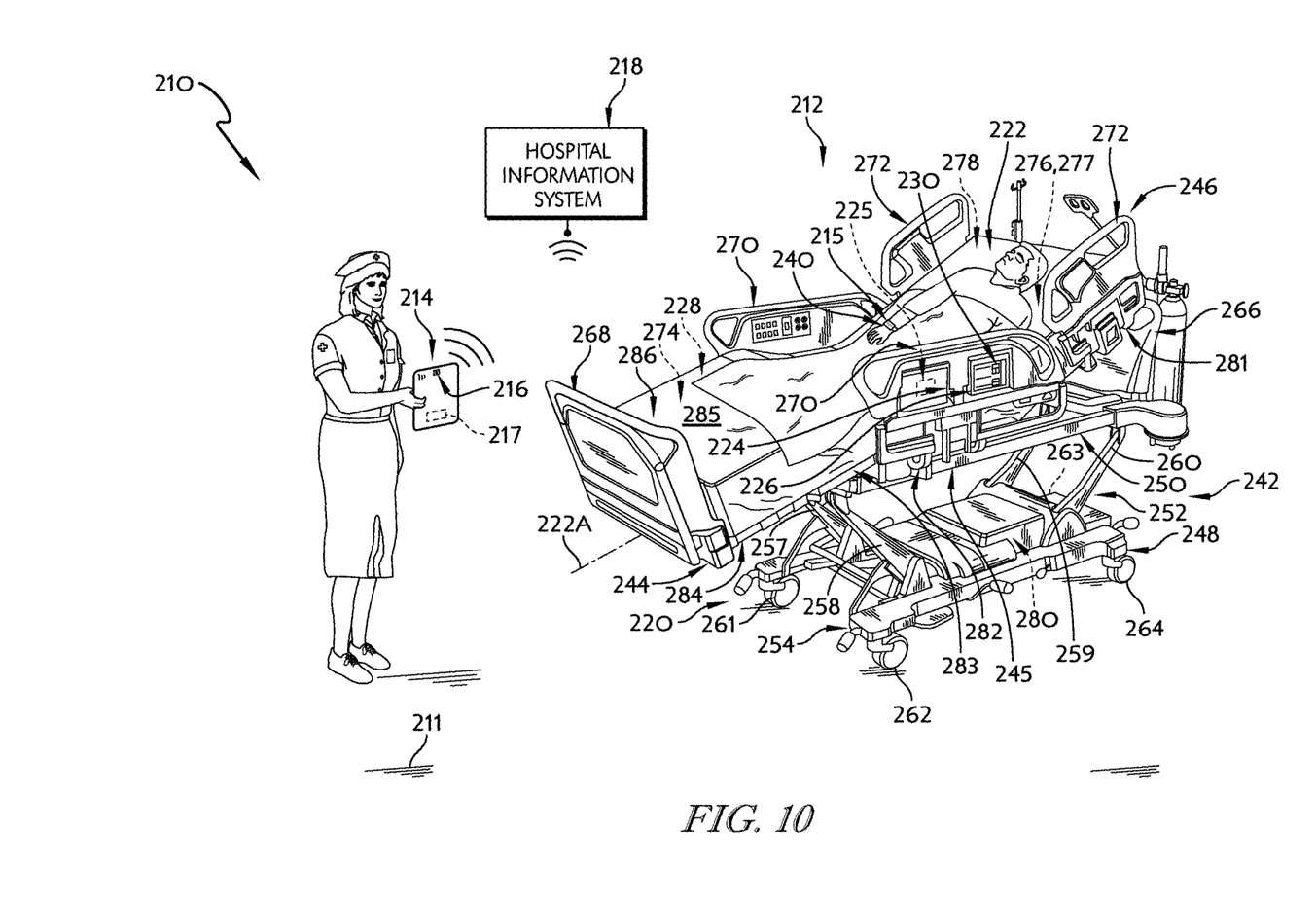
FIG. 10 is a perspective view of another care system including a patient support system, a mobile computing device, and a information system configured to employ near field communication units to transfer information from the patient support system to the mobile computing device.

Another illustrative care system 210 is shown in FIG. 10. The care system 210 is substantially similar to the care system 10 shown and described with regard to FIGS. 1-9. Accordingly, similar reference numbers in the 200 series indicate features that are common between the care system 10 and the care system 210. The description of the care system 10 is hereby incorporated by reference to apply to the care system 210, except in instances when in conflicts with the specific description and drawings of the care system 210.

Unlike the care system 10, the mobile computing device 214 of the care system 210 is a tablet computer including a reader (camera) 216 and a near field communication (NFC) unit 217 as shown in FIG. 10. Further, the control system 224 of the care system 210 includes a complementary near field communication (NFC) unit 225 integrated into a siderail 270 as shown in FIG. 10. Communication between the NFC units 217, 225 of the mobile computing device 214 and the patient support system 212 is configured to provide an another mode of communicating information from the patient support system 12 to the mobile computing device 214. In some embodiments of the care system 210 with NFC units 217, 225, the data graphic generation functionality may be left out of the care system 210 entirely.

Although certain illustrative embodiments have been described in detail above, variations and modifications exist within the scope and spirit of this disclosure as described and as defined in the following claims.

The invention claimed is:

1. A patient support system comprising
a reconfigurable patient support apparatus, and
a control system including a controller, a user input coupled to the controller, and a display coupled to the controller, the controller configured
  (i) to receive a request for information output,
  (ii) to determine whether patient information has been received by the control system,
  (iii) to display a patient information entry screen on the display if the patient information has not been received by the control system,
  (iv) to receive the patient information or receive a signal indicating that the requested patient information will not be input,
  (v) to aggregate information corresponding to the patient support apparatus and the patient information,
  (vi) to generate a bar code including information corresponding to
    (a) the configuration of the patient support apparatus,
    (b) the location of the patient support apparatus in a care facility, and
    (c) the aggregated information and
  (vii) to display the bar code on the display.

2. The patient support system of claim 1, wherein the patient support apparatus includes a lower frame, an upper frame, and a lift system coupled between the lower frame and the upper frame, the lift system is configured to move the upper frame relative to the lower frame, and the bar code includes information corresponding to the position of the upper frame relative to the lower frame.

3. The patient support system of claim 2, wherein the patient support apparatus includes a deck including a seat deck section coupled to the upper frame and a head deck section movable from a first position to a second position relative to the seat deck section, and the bar code includes information corresponding to the position of the head deck section relative to the seat deck section.

4. The patient support system of claim 3, wherein the patient support apparatus includes a siderail and movable from a raised position to a lowered position, and the bar code includes information corresponding to the position of the siderail.

5. The patient support system of claim 4, wherein the patient support apparatus includes a headrail coupled to the head deck section and movable from a raised position to a lowered position relative to the head deck section, and the bar code includes information corresponding to the position of the headrail relative to the head deck section.

6. The patient support system of claim 1, wherein the patient support apparatus includes a footboard movable between a first position coupled to the deck and a second position spaced apart from the deck, and the bar code includes information corresponding to the position of the footboard relative to the deck.

7. The patient support system of claim 1, wherein the patient support apparatus includes a plurality of wheels and a brake system movable from a braked position resisting movement of at least one wheel to an unbraked position allowing movement of at least one wheel, and the bar code includes information corresponding to the position of the brake system.

8. The patient support system of claim 1, wherein the patient support apparatus includes at least one sensor configured to detect patient data corresponding to a patient supported on the patient support apparatus, and the bar code includes information corresponding to the patient data.

9. The patient support system of claim 7, wherein the at least one sensor includes a scale coupled to the controller and configured to detect patient weight of a patient on the patient support apparatus, and the bar code includes information corresponding to the patient weight.

10. The patient support system of claim 1, wherein the bar code is one of a linear barcode, a matrix barcode, and a quick response code.

11. The patient support system of claim 1, wherein the controller is configured to receive information corresponding to the location of the patient support apparatus in the care facility from the user input.

12. A patient support system comprising
a patient support apparatus, and
a control system including a controller, a user input coupled to the controller, and a display coupled to the controller,
wherein the controller is configured to perform a program in which the control system:
(i) receives a request for information output,
(ii) determines whether patient information has been received by the control system,
(iii) displays a patient information entry screen on the display if the patient information has not been received by the control system,
(iv) receives and confirms the patient information or receives a signal indicating that the requested patient information will not be input,
(v) aggregates information corresponding to the patient support apparatus and the patient information,
(vi) generates a bar code including the aggregated information, and
(vii) displays the bar code on the display.

13. The patient support system of claim 12, wherein the bar code is a matrix barcode.

14. The patient support system of claim 12, wherein the bar code is a quick response code.

15. The patient support system of claim 14, wherein the information from the user input corresponds to a patient supported on the patient support apparatus.

16. The patient support system of claim 15, wherein the information from the user input includes at least one of patient pain level, patient respiratory rate, patient heart rate, patient current medications, and patient blood pressure.

17. The patient support system of claim 12, wherein the control system is configured to skip instructions (iii) and (iv) if the patient information has been previously received by the control system in instruction (ii).

18. The patient support system of claim 17, wherein the control system is configured to receive patient information from the user input.

19. The patient support system of claim 17, wherein the control system is configured to receive patient information from a static data graphic associated with the patient.

* * * * *